US007914741B2

(12) United States Patent
Williams et al.

(10) Patent No.: US 7,914,741 B2
(45) Date of Patent: Mar. 29, 2011

(54) AUTOMATED MICROSAMPLING DISSOLUTION TEST SYSTEM

(75) Inventors: Archibald Williams, Wareham, MA (US); Lawrence Dwayne Chin, Needham, MA (US); Martin Schwalm, Lakeville, MA (US); Brett Andrew Feeney, Grafton, MA (US); Timothy Noone, Simsbury, CT (US); Thomas John Calef, West Bridgewater, MA (US)

(73) Assignee: Agilent Technologies, Inc., Santa Clara, CA (US)

( * ) Notice: Subject to any disclaimer, the term of this patent is extended or adjusted under 35 U.S.C. 154(b) by 436 days.

(21) Appl. No.: 12/008,281

(22) Filed: Jan. 10, 2008

(65) Prior Publication Data
US 2008/0226499 A1    Sep. 18, 2008

Related U.S. Application Data

(60) Provisional application No. 60/884,238, filed on Jan. 10, 2007, provisional application No. 60/884,242, filed on Jan. 10, 2007, provisional application No. 60/884,252, filed on Jan. 10, 2007, provisional application No. 60/884,253, filed on Jan. 10, 2007, provisional application No. 60/961,636, filed on Jul. 23, 2007, provisional application No. 61/003,258, filed on Nov. 15, 2007.

(51) Int. Cl.
*G01N 33/00* (2006.01)
*G01N 33/48* (2006.01)
(52) U.S. Cl. ............... 422/68.1; 422/63; 422/65; 422/1; 422/3; 422/28; 422/81; 422/100; 422/102; 422/103; 422/66; 422/67; 422/99; 366/91; 366/95; 73/866

(58) Field of Classification Search .................. 422/1, 3, 422/28, 33, 50, 68.1, 81, 100, 102, 103
See application file for complete search history.

(56) References Cited

U.S. PATENT DOCUMENTS

| 4,279,860 | A |   | 7/1981 | Smolen |
|---|---|---|---|---|
| 4,335,438 | A |   | 6/1982 | Smolen |
| 4,924,716 | A | * | 5/1990 | Schneider ...................... 73/866 |
| 5,589,649 | A | * | 12/1996 | Brinker et al. .................. 73/866 |
| 5,816,701 | A | * | 10/1998 | Martin et al. ................. 366/208 |
| 6,170,980 | B1 | * | 1/2001 | Martin .......................... 366/191 |
| 6,174,497 | B1 | * | 1/2001 | Roinestad et al. ......... 422/82.05 |
| 6,303,909 | B1 | * | 10/2001 | Fernando et al. ............. 219/429 |
| 6,948,389 | B2 |   | 9/2005 | Brinker et al. |
| 6,962,674 | B2 |   | 11/2005 | Dean et al. |

OTHER PUBLICATIONS

United States Pharmacopoeia, vol. 24, Ch. 711, pp. 1941-1944 & Ch. 724, pp. 1941-1951 (1998).

* cited by examiner

*Primary Examiner* — Brian J Sines

(57) ABSTRACT

A dissolution testing apparatus includes a base structure, a vessel support structure, a cleaning manifold and a stirring mechanism. The vessel support structure is configured for mounting testing vessels and is rotatably mounted to the base structure. The vessel support structure is rotatable from an upright position at which respective open ends of the vessels face upwardly to an inverted position at which the open ends face downwardly. The cleaning manifold is mounted to base structure below the vessel support structure and is configured for directing a fluid into the vessels while the vessel support structure is at the inverted position. The stirring mechanism includes shafts and is movably mounted to the base structure. The stirring mechanism is movable from a lower position at which the shafts extend into the vessels to an upper position at which the shafts are outside the vessels. At the upper position the stirring mechanism provides clearance for the vessel support structure to rotate.

13 Claims, 20 Drawing Sheets

AUTOMATED MICROSAMPLING DISSOLUTION TEST SYSTEM

PRIORITY CLAIM

This application claims priority from provisional applications 60/884,238 filed Jan. 10, 2007, 60/884,242 filed Jan. 10, 2007, 60/884,252 filed Jan. 10, 2007, 60/884,253 filed Jan. 10, 2007, 60/961,636 filed Jul. 23, 2007, and 61/003,258 filed Nov. 15, 2007.

BACKGROUND OF THE INVENTION

Dissolution testing is an analytical technique used to determine the rate at which a pharmaceutical dosage form, usually a tablet, capsule, or transdermal, dissolves into a given media over time. Generally, the release (or dissolution), of the Active Pharmaceutical Ingredient (API) from the dosage into the media is measured for a specified duration under controlled conditions. This measurement is made either by performing in situ measurements with fiber optic probes, or samples are taken at predetermined time points, filtered, and measured on an analytical instrument, most commonly, an HPLC or in-line UV analyzer. The release of API may be rapid, (within minutes), for immediate release dosage forms, or may be significantly longer, (occurring over hours or weeks) for controlled/modified release formulations.

Conventionally constructed dissolution apparatus most commonly employ a solid base; a vessel manifold mounted on said base which is connected to a circulating, temperature programmable water bath; and a stirring element, which is rotated (or reciprocated) within the vessel. Automated dissolution testing systems generally contain additional dosage, media, and sample handling systems. Requirements for a dissolution testing apparatus are provided in United States Pharmacopeia (USP), Section 711, Dissolution (2000). The underlying process of dissolution testing and apparatus for performing such testing are known in the art.

SUMMARY OF THE INVENTION

The Microsampling dissolution testing system or apparatus is comprised of a base structure; a plurality of vessels mounted on an invertible, temperature controlled bath; a cleaning mechanism; an agitation mechanism for each vessel; a plurality of hydrodynamic, nonresident sampling probes mounted on a sampling mechanism; a non-resident dispensing manifold; a novel fluid handling system; a MicroSampler; a sample transfer mechanism; and a sample and filter storage apparatus.

In this invention, the base structure of the dissolution system or apparatus is comprised of a wash bin, a collection grate, a vessel cleaning manifold, a bath mounting assembly, a locking mechanism, dispensing manifold tracks, and stirring and sampling assembly tracks.

In accordance with the present invention, a temperature controlled bath is mounted to a mounting assembly. In the preferred configuration of the present invention, the bath mounting assembly is a rotary motor that enables the temperature controlled bath 360° of rotation along the horizontal axis. In addition, the base structure preferably incorporates a locking mechanism to secure the bath in a proper position (as defined by USP guidelines for dissolution) during testing. For example, a plurality of pneumatic locking pins may extend from the base of the system and insert said pins into a plurality of receiving cavities or bores thereof located linearly whereby said locking pins and cavities interlock the rotatable bath.

In accordance with the present invention, the temperature controlled bath is comprised of three major components; a plurality of cavities for mounting a plurality of dissolution vessels; a plurality of watertight vessel mounting covers for centering and sealing said dissolution vessels within said bath; and a self-contained vessel heating device for maintaining temperature uniformity within said dissolution vessels. The plurality of cavities contained within the bath enable mounting of a plurality of dissolution vessels wherein adaptors may be preferably incorporated to accommodate a wide array of vessel sizes and manufacturer designs. In the preferred embodiment of the disclosed invention, each mounted vessel contains a vessel cover, which incorporates a watertight sealing means such as an o-ring. The sealing means should sufficiently seal the mounted vessels within the bath such that when the bath is inverted during a cleaning cycle, there is no possibility of material leaking from said bath. In the preferred configuration of the disclosed invention, the vessel heating device is a submersible heating coil which intercalates the dissolution vessels and maintains the temperature of the surrounding media contained within the bath. In an alternative embodiment of the disclosed invention the vessel heating device may include strip heaters contained within the bath assembly, temperature controllable solid or semisolid heating blocks, a plurality of heating coils, or other heating means that are consistent with the spirit of the disclosed invention.

In accordance with this invention, a novel vessel cleaning system is employed to effectively dispose of spent test solution and insoluble dosage excipients, thereby eliminating carryover or cross-contamination. As previously mentioned, the disclosed invention includes a means to invert the dissolution vessels that are mounted on the bath such that the open side of said vessels are configured to face downward toward the cleaning manifold when inverted. The preferred configuration of the present invention is designed such that when the bath is rotated 180°, the spent test media, dissolved dosages, and testing devices are gravimetrically emptied from the dissolution vessels into a collection grate which is horizontally positioned above the wash bin and are both mounted on the base of the system. In this manner, the collection grate preferably contains a plurality of fissures to allow liquid media and dissolved material to flow through said grate to the wash bin which incorporates a waste port in said wash bin. In accordance with this invention, the collection grate is preferably constructed with a plurality of dedicated cavities in which the nozzles of the cleaning manifold extend through said collection grate and are positioned beneath the plurality of inverted dissolution vessels. In this manner, the collection grate is preferably formed to collect and accumulate dosage sinkers or baskets towards an accessible position of the system wherein an access door is mounted to the base structure.

In accordance with the present invention, the disclosed apparatus of the present invention incorporates a vessel cleaning manifold. The cleaning manifold incorporates a plurality of spraying nozzles that extend through cavities within the collection grate wherein said nozzles are positioned to spray water, cleaning fluid or air into the interior of the inverted dissolution vessels. In the preferred configuration of the disclosed invention, the cleaning manifold may also include a series of programmable switches or valves that enable cleaning of the vessels with a variety of fluids and air.

In accordance with the present invention, a dispensing manifold for dosage handling and fluid dispensing is horizontally mounted to the dispensing manifold tracks of the system base. The dispensing manifold in particular is a nonresident dispensing manifold wherein the manifold is positioned over the dissolution testing vessels during the media filling and dosage dispensing process. In this manner, a plurality of fluid dispense nozzles are mounted on the ventral side of the manifold wherein said nozzles are positioned above the plurality of dissolution vessels that are mounted to the bath. In accordance with this invention, a dosage carousel constructed of a fixed portion containing a single bore and a rotatable portion containing a plurality of cavities is rotatably mounted to said fixed portion thereof said carousel is mounted on the dorsal side of the manifold wherein an extended cylinder, herein referred to as a dosage dropper, is inserted into said bore within said carousel. In this manner, when the rotatable portion of the carousel rotates one position such that a cavity of the rotatable portion of the carousel aligns with the bore of the fixed portion of said carousel, a single dosage drops through the bore within the dosage carousel and dosage dropper into the vessel containing media. In the preferable configuration of the disclosed invention, the manifold is horizontally displaced along a manifold track such that it is moved away from the dissolution vessels during testing. The stirring and sampling assembly is subsequently lowered into the dissolution vessel and a plurality of paddles is rotated at a specified speed for a specified duration.

In an alternate mode of operation, the dosage carousels may be replaced with a plurality of specialized basket carousels. In accordance with the present invention, the basket carousels contain a plurality of cavities wherein said cavities adopt a cylindrical shape to hold standard dissolution testing baskets and are rotatably mounted to the dispensing manifold. In this manner, a specialized o-ringed shaft that is contiguous with the stirring assembly is incorporated such that it may be lowered into an aligned basket until the o-ring of the shaft creates a seal and is temporarily attached with the rim of said basket, wherein said shaft and basket may then be raised from the carousel and the manifold may be horizontally displaced along a manifold track, and the basket may be subsequently lowered into the dissolution vessel and rotated at a specified speed for a specified duration. In accordance with this invention, a basket removal mechanism is incorporated, where said removal mechanism is preferably mounted to the obverse face of the dispensing manifold. In this manner, when aligned, the removal mechanism forms a clasp around the baskets that are attached to the specialized basket shafts and separates said baskets and shafts wherein said baskets are gravimetrically displaced into the dissolution vessels.

In this invention, the stirring and sampling assembly is comprised of two main components, a stirring mechanism and sampling mechanism. The stirring mechanism contains a plurality of fixed shafts in which said shafts are rotatably mounted to the stirring and sampling assembly and may be affixed with paddle or specialized basket shafts. In the preferred configuration of the disclosed invention, the fixed shafts are synchronously rotated at a predetermined speed for a specified duration by a programmable motor and driver means. In an alternative configuration of the disclosed invention, the system may incorporate a plurality of motors and drivers for individual shafts. In accordance with this invention, the sampling mechanism is mounted to the stirring and sampling assembly and preferably incorporates an additional motor and driver means wherein the sampling probes are lowered into the dissolution vessels, aspirate a sample, and raise said probes out of said vessels after sampling.

In this invention, the sampling probe geometry is constructed in accordance with a hydrodynamic shape that minimizes disturbance to the laminar flow within the dissolution vessels when sampling whereby velocity differentials between the leading and lagging edge of the probe are effectively reduced. In this manner, the probe may be constructed to adopt an oval, elliptical, or tear-drop shape. In the preferable configuration of the present invention, the sampling probe is constructed to incorporate additional temperature and pH probes or sensors. In the present embodiment of the disclosed invention, the probe may be formed as one contiguous structure; or in alternate embodiments of the disclosed invention, the probe may be three separate pieces that are fused and shaped. In addition, the sampling probe may optionally include a shaped pre-filter to preclude solid material from clogging the sampling probe, sampling lines, or pump.

In accordance with the present invention, an image capturing device for monitoring the dissolution test is preferably incorporated. In the preferred configuration of the present invention, the image capturing device is mounted to the bath such that it is able to visually capture and record the dissolution tests. In alternate configurations, the image capturing device may be mounted to the base or auxiliary components of the system. The image capturing device includes at least one means for capturing real-time video or still images that are preferably streamed to a recording device. In addition, the video or image is preferably time stamped and indexed to match the testing data. The means for capturing the video or still images may be a single image capturing device or a plurality of devices. For example, a camera may be provided at each of the testing vessels to record the process therein.

In accordance with the present invention, a novel sample collection and filtration apparatus which will be referred to herein as a MicroSampler is incorporated. The MicroSampler is comprised of a sampling means, a sample dispensing mechanism, a filter holding mechanism, a sample pre-flush assembly, a sample collector holding mechanism, and a mechanism for forcing a plurality of aspirated samples through said filter to said holding mechanism.

In the preferred embodiment of the disclosed invention, the sampling means is a peristaltic pump containing a plurality of channels, wherein each channel is dedicated to a single dissolution test vessel. In this manner, sample tubing is installed in each channel and connected to a sampling probe that is mounted on the stirring and sampling assembly and an indexable dispensing mechanism that is mounted to the MicroSampler. In accordance with this invention, the indexable dispensing mechanism is attached to the MicroSampler wherein said dispensing mechanism may align itself with dedicated, pre-programmed positions of the filtration and collection mechanisms throughout the dissolution test.

In the present invention, the MicroSampler incorporates a filter holding mechanism that is capable of positioning the filter assembly disclosed herein. In accordance with this invention, the MicroSampler preferably incorporates a filter pre-flush assembly that is preferably mounted to said MicroSampler on a sliding means wherein said pre-flush assembly may be horizontally displaced from said filter. In accordance with this invention, the pre-flush assembly is preferably configured with a plurality of bores capable of collecting and dispensing to waste samples or portions of sample that are passed through the filters. In addition, the pre-flush assembly may incorporate a vacuum or pressure means for more efficiently collecting samples that are flushed through the filter assembly.

In accordance with the present invention, the MicroSampler incorporates a collection assembly. The collection assembly preferably incorporates a sample assembly holder that ensures proper alignment of the filter assembly and sample assembly. In the preferred configuration of the present invention, the collection assembly is movably mounted to the MicroSampler wherein the sample and filter assemblies are engaged and disengaged as described below.

In the present invention, the Microsampler incorporates a novel filter plate assembly is provided for receiving, filtering and retaining a plurality of samples taken during dissolution testing. Generally, the filter plate assembly of the present invention is configured in two parts. The upper filter plate receives and filters a plurality of samples and is then engaged with the lower sample well to deposit the samples therein. The upper filter apparatus, which may be a plate, cartridge, or individual filter, receives and filters the samples and is then engaged with the lower sample collection apparatus to deposit the samples therein. The sample collection apparatus preferably further includes a seal arrangement disposed on top of a sample collection well or vial. The dispensing end of the upper filter plate pierce through the resilient seals to allow deposit of the samples into the sample collection wells. However, when the upper filter plate is withdrawn the seals close. The filter and collection apparatus configuration also allows for a compact, orderly and addressable format for the collected samples which is advantageous for interfacing with an analytical instrument and for storage of the samples.

In accordance with the present invention, a sample and filter transfer means is preferably used in conjunction with the MicroSampler and interfaces with an analytical instrument and hotel. The sample transfer means may include a robot, a conveyer, or other apparatus that is capable of removing used filter and sample collection apparatuses and replacing said apparatuses. In this manner, the samples may be subsequently transferred from the MicroSampler and placed in an analytical testing instrument for analysis or a hotel for storage, whereas the spent filter apparatus may be subsequently placed in the hotel or a designated waste means, while a new collection and filter apparatus may be acquired from the hotel and placed in the MicroSampler for the next dissolution test.

In accordance with this invention, a novel fluid handling system is preferably incorporated. In the disclosed configuration of this invention, liquid media is pumped from bulk containers, the liquid volume is gravimetrically confirmed, and is then pumped into a plurality of holding vessels. The preferred configuration of the present invention has one dedicated holding vessel for each dissolution vessel. The holding vessel stores pumped media and maintains a preset temperature until it is time to dispense it into its respective dissolution vessel. When media is dispensed from the holding vessels, it is dispensed in parallel through dispense valves and tubing that are dedicated to each dissolution vessel. In addition, a temperature controller is preferably incorporated for each holding vessel in order to maintain media temperature uniformity at the predetermined testing temperature. The holding vessel temperature controllers ensure that media is pre-equilibrated prior to dispensing it in the test vessels. As a result, media equilibration time is minimized and temperature fluctuation is virtually eliminated. This mitigates the potential adverse impact with temperature sensitive formulations and APIs, and minimizes the downtime between media changes.

In one implementation, a dissolution testing apparatus includes a base structure, a vessel support structure, a cleaning manifold and a stirring mechanism. The vessel support structure is configured for mounting a plurality of testing vessels and is rotatably mounted to the base structure. The vessel support structure is rotatable from an upright position at which respective open ends of the testing vessels face upwardly to an inverted position at which the open ends face downwardly. The cleaning manifold is mounted to base structure below the vessel support structure and is configured for directing a fluid into the testing vessels while the vessel support structure is at the inverted position. The stirring mechanism includes a plurality of shafts and is movably mounted to the base structure. The stirring mechanism is movable along a vertical direction from a lower position at which the shafts extend into the respective vessels to an upper position at which the shafts are outside the testing vessels. At the upper position the stirring mechanism provides clearance for the vessel support structure to rotate from the upright position to the inverted position.

DETAILED DESCRIPTION OF THE PREFERRED EMBODIMENT

Turning to FIG. 1, a flow chart has been drawn according to the described invention disclosed in the preferred embodiment. In the diagram pumps are denoted by P, valves by V, holding vessels by H, and dissolution vessels by D for parsimony. All arrows illustrate the preferable flow path and mode best known of the described invention.

Four-way valve (V1) 6 controls the flow of liquid from bulk vessel 1, weighing vessel 4, and wash fluid 15 that are pumped through fluid lines by way of fluid handling pumps 2, 5 and 16, or respectively; to the holding vessels 17-24 or purged to waste 47. Two-way valves 7-13 act independently and control the flow of liquid to the holding vessels 17-23, respectively. Three-way valve 14 controls the flow of liquid between holding vessel 24 and the purge line 47. Holding vessels 17-24 are insulated by a temperature controller 25 at a preset testing temperature and the flow of liquid media is controlled by two-way valves 26-33. Valves 26-33 act in parallel such that when media is dispensed from holding vessels 17-24 into dissolution vessels 34-41, it is done synchronously. Waste pump 48 controls the flow of liquid media for aspirating fluid from dissolution vessels 34-41 to waste.

In normal operating mode, a bulk container 1 holds liquid media that is dispensed into weighing vessel 4 by pump 2 and the volume is confirmed by a scale 3. After the volume disponsed into weighing vessel 4 has been confirmed, it is pumped by pump 5 through valve 6 to a predetermined holding vessel 17-24. The holding vessels 17-24 are controlled by a series of valves 7-14, respectively. For example, if one wanted to add liquid media from bulk container 1 to holding vessel 24, the media would follow the aforementioned path and valve 14 would switch to the fill position, thereby dispensing liquid media from bulk container 1 to holding vessel 24. This action would be repeated for all holding vessels that were designated to be filled with liquid media from bulk container 1. The holding vessels that will be filled with liquid media from bulk container 1 are predetermined and input in a software program before starting an experiment. The liquid media that was dispensed into the designated holding vessel (s) is then incubated by temperature controller 25.

After all the holding vessels that were designated to contain liquid media from bulk container 1 were filled, the common lines are cleaned. The wash pump 16 pumps wash fluid from wash fluid vessel 15 through the common lines to purge waste 47. Four-way valve 6 and three-way valve 14 are in the purge position when fluid lines are flushed with was fluid.

An additional fluid line flush with the subsequent liquid media may also be performed by switching valve 6 from the wash position to a designated bulk container position and valve 14 would remain in the purge position. For example, if one wanted to flush the common lines with liquid media from bulk container 42 prior to filling holding vessels with liquid media; then a predetermined volume of liquid media would be pumped from the bulk container 42 to weighing container 45. The liquid media would then be pumped by pump 46 through valve 6 to the purge waste 47 until it was confirmed by scale 44 that weighing vessel 45 was completely empty. After the common lines were completely flushed, valve 14 would switch to a closed position.

To fill designated holding vessels with liquid media from bulk container 42, the normal mode of operations is identical to that as described for bulk container 1 where bulk container 1 is replaced by bulk container 42; pump 2 is replaced by pump 43; scale 3 is replaced by scale 44; weighing vessel 4 is replaced by weighing vessel 45; and pump 5 is replaced by pump 46. In addition, valve 6 is switched to open the fluid path from bulk container 42.

In an alternative embodiment of the disclosed invention, a plurality of bulk containers, scales, weighing vessels, and pumps are incorporated to increase flexibility of experimentation. Valve 6 is replaced with a valve that enables additional flow paths or a series of valves may be incorporated to accommodate alternative configurations and instrumentation.

In the preferred embodiment of the invention, holding vessels may be filled at any time before, after, or during a dissolution test, enabling preheated (-cooled) liquid media to be dispensed on demand. For example, during an experiment, when a predetermined amount of time has passed, two-way valves 26-33 synchronously open, dispensing media from holding vessels 17-24 to dissolution vessels 34-41, respectively, in parallel. Because the media was preheated (-cooled) to the dissolution test temperature, the experiment is able to resume without a temperature incubation period.

After a dissolution test is complete, media can be removed from the dissolution vessels using specialized non-resident sampling probes and waste pump 48. The used media is pumped to a common or designated waste container/drain and the vessels are automatically cleaned. Before or during the cleaning procedure, holding vessels are filled with media as previously described. After the cleaning procedure is complete, preheated liquid media is dispensed from holding vessels 17-24 to dissolution vessels 34-41 and a subsequent dissolution test may begin.

In an alternate embodiment of the disclosed invention, specialized sampling probes and pumps 48 may be used to remove media from the dissolution vessels 34-41 when necessary.

Turning to FIG. 2 and FIG. 3, the dissolution testing apparatus of the present invention generally includes a temperature controllable bath manifold 50 that is configured to receive and retain an array of testing vessels 51 therein. The testing vessels 51 contain the doses and solution being tested. The bath manifold 50 includes a vessel support structure (or vessel plate) 94 that provides locations for mounting the testing vessels 51. Thus, the vessel support structure 94 includes a plurality of cavities through which respective testing vessels 51 are inserted to support the testing vessels 51. The bath manifold 50 is positioned above a collection grate 54, wash bin 52, and plurality of spray heads extending from the cleaning manifold 53 configured wherein said spray heads are aligned to direct jets of water, cleaning fluid, and air upwardly to clean the inverted testing vessels 51 in a manner that will be more fully described below. Finally, the wash bin 52 incorporates a collection grate 54 positioned therein to catch and retain any objects such as baskets, sinkers or other objects that may be contained within the testing vessels 4 and dumped into the wash bin 52 upon their inversion. The dissolution testing apparatus includes a base structure 96 configured as needed for supporting the various components of the dissolution testing apparatus.

FIG. 3 illustrates an enlarged view of the bath manifold of the present invention. It can be seen that upon completion of the testing cycle, the apparatus either withdraws the stirring paddles and sampling probes from the testing vessels 51 or lowers the bath manifold 50 so that the vessels 51 are positioned clear of the stirring and sampling assembly. The bath manifold 50 (including the vessel support structure 94) then rotates 180° around a horizontal axis into the position depicted in FIG. 4. The rotation of the bath manifold 50 and vessel support structure 94 causes the testing vessels 51 to be positioned in an inverted fashion over the wash bin 52 causing any test fluid and non-dissolved doses contained therein, and any objects such as baskets, sinkers, or other objects that may have been contained within the testing vessels to be emptied into the wash bin 52. The spray nozzles of the cleaning manifold 53 then direct jets of water, cleaning fluid, or air into the testing vessels 51 to rinse out any residual testing solution or non-dissolved doses and thoroughly clean the said vessels 51. The testing fluid and wash fluid drains from the testing vessels 51 through the collection grate 54, to the wash bin 52, which is molded to gravimetrically direct fluid to a common waste port. Upon completion of the washing cycle, the bath manifold 50 again rotates 180° thereby returning the testing vessels 51 to an upright position, as depicted in FIG. 2, thereby resetting the test vessels to begin a new cycle of dissolution testing.

The present disclosure thus provides a system, apparatus and method capable of resetting the testing vessels automatically thereby allowing recycling of the dissolution testing apparatus without the need for operator intervention. In this manner, part of the novelty of the present invention resides in the ability to empty and clean the testing vessels. Accordingly, other structures and arrangements that provide for at least partial inversion (i.e. less than a total 180° inversion) to dump the remaining test solution from the vessels should be considered to fall within the scope of the present invention. Further, systems that utilize any fluid to clean the vessels including solvents, water, compressed air and combinations thereof also are presumed to fall within the scope and intent of the present disclosure.

Turning to FIG. 5, it can be seen that in the present invention, in contrast with those of the prior art, additional features are required to enable the novel fluid handling, cleaning, sampling and dispensing mechanisms. The dissolution testing apparatus includes a stirring and sampling assembly 55. As noted above, the stirring and sampling assembly 55 includes a stirring mechanism that includes a plurality of shafts 95. The shafts 95 may include respective paddles 67 or the shafts 95 may be basket shafts as appreciated by persons skilled in the art. The stirring and sampling assembly 55 also includes a sampling mechanism that may include sampling probes as described below. In order to reset the testing vessels 51 through inversion, the stirring and sampling assembly 55 and dispensing manifold 56 need to be moved away from the bath manifold 50. In the prior art, this was not an issue because as a result of the temperature controlled water bath manifold being stationary, all of these ancillary assemblies could be installed onto a header that rested on top of the vessels. To overcome the need for creating movable assemblies to accommodate inversion of the testing vessels 51, the present invention utilizes moving headers that allow the stirring and sampling assembly 55 to be displaced vertically relative to the bath manifold 50. Further, an automatic dispensing manifold 56 is provided that is configured to add indexed doses into the testing vessels 51 by moving laterally to an indexed position over the testing vessels 51, dropping a dose and then returning to its starting position, thereby reliably loading a dose into the testing vessel 51 and moving out of the way so that the stirring and sampling assembly 55 can be reengaged with the testing vessel 51. The automatic dispensing manifold 56 of the present invention is laterally displaceable along tracks 57 thereby allowing the dispensing manifold 56 to move into an indexed position over the vessels 51 and then return to a storage position displaced from the vessels 51.

Turning to FIG. 6, a plurality of dosage carousels 58 are disposed and arranged on the dispensing manifold 56 in a manner that corresponds to and matches the arrangement of testing vessels 51 in the bath manifold. Each of the automatic dosage carousels 58 includes a plurality of movable cavities 59 therein such that each cavity 59 within the carousel 58 receives and contains one dose. A stepping motor controls the movement of the automatic dosage carousels to selectively move the carousel 58 to align one of the cavities with the dosage dropper 60 in the dispensing manifold. When the cavity 59 containing a dose is positioned over the dosage dropper 60, the dose is allowed to drop therethrough and into the dissolution vessel 51 below to commence a subsequent testing operation.

In operation, the dispensing manifold 56 first slides into position over the dissolution vessels 51, the stepping motor operates to move the carousels 58 one position thereby exposing a cavity 59, containing a dose to the dosage dropper 60 in the dispensing manifold 56 positioned over the vessel 51, the dose drops into the testing vessel 51 and the dispensing manifold 56 slides back to its home position. The carousels 58 may be rotatable devices as are depicted in the figures. Further the carousels 58 may be linearly displaceable. It is also possible that the carousels 58 are arranged horizontally or vertically as these are merely design choices related to the size or type of dose being tested.

It can also be seen in referring to FIG. 7 and FIG. 8 in particular, that the cavities of the carousels 58 and basket carousels 62 include a fixed portion that is mounted to the dispensing manifold 56, a rotatable portion 64 mounted to said fixed portion, and a shoulder 59 along the sidewalls thereof. The shoulder 59 is provided in order to receive and retain dosages, dosages with sinkers, and baskets 63 such as are also commonly utilized in the art. In this regard, the shoulders 59 prevent the baskets 63 from shifting in the basket carousel 62 and dosages from moving within the carousels 58 to assure proper alignment when acquiring a basket or dropping a dosage respectively. Additional inserts may be incorporated with dosage carousels wherein said dosages are formed in non-conventional shapes and have a propensity to shift within said carousels. In addition, covers or lids may be further incorporated for both types of dosage carousels described herein.

FIG. 9 is a sectional view of a conventionally constructed dissolution testing apparatus. The apparatus is shown running a dissolution test with a paddle type apparatus 67 and the sampling probe 65 is shown inserted into the dissolution vessel 51. In the preferred embodiment of the present invention, the sampling probe 65 is coupled to a sampling bar 66 that is operatively attached to the stirring and sampling assembly 55 wherein said sampling probes 65 may be lowered and raised from the dissolution bath during testing.

Turning to FIG. 10, the sampling probe 67 is preferably comprised of at least two distinct ends, a shaped sampling end 68 and a connector end 69 that creates a water tight seal with sample tubing 70. During a dissolution test, the sampling end 68 of the sampling probe 67 is inserted into the dissolution test vessel 51. A sample is aspirated from the sampling end 68, through the probe 67, and through the tubing that is generally coupled to a sample collection apparatus or sample analyzer.

FIG. 11 depicts a plan view of different probe shapes that may be adopted for the sampling probe. The shapes shown are a tear-drop 71, oval 72, and ellipse 73. The leading edge of the probes, which is described by the edge that faces the direction of fluid flow, are preferably rounded in shape to ensure that laminar flow is not disturbed during sampling.

Turning to FIG. 12, the probe may also include a pre-filter 74 that is attached to the sampling end of the probe 68. The pre-filter 74 preferably adopts that same hydrodynamic shape of the sampling probes.

FIG. 13 is a 2-dimensional plot of vorticity maps for a conventionally constructed sampling probe used with automated dissolution testers and the sampling probe disclosed in the present invention. The plot for the conventionally constructed sampling probe demonstrates the influence of the sampling probe on the laminar flow when it is inserted during dissolution testing. Alternatively, the plot for the disclosed invention demonstrates that the hydrodynamically shaped sampling probe does not affect the laminar flow when sampling during dissolution testing.

In FIGS. 14-18, the filter plate assembly of the present invention is illustrated and generally indicated as 75. As will hereinafter be more fully described, the filter plate assembly 75 has a unique configuration that allows secure and reliable transfer of the samples taken while also facilitating the use of reduced sample sizes including samples having a sample size as small as 1 µl.

Turning to FIG. 14 and FIG. 15, the filter plate assembly 75 can be seen to include an upper filter plate 76 and a lower sample well array 78. A seal 79 component as will be discussed in further detail below can be seen installed on top of the lower sample well array 78. The upper filter plate 76 can be seen to include an array of bores 77 having openings at the top ends thereof. The bores 77 extend downwardly and terminate in a hollow dispense tip 80 (FIG. 16). The dispense tip 80 is preferably sharp enough to be effective at piercing the seal 79 located on top of the lower sample well array 78 as will be discussed in detail below. The upper filter plate 76 is preferably formed from a polymer material and is more preferably injection molded. Further, the dispense tip 80 may also be polymer or may be formed from metal.

Turning now to FIGS. 17 and 18, it can be seen that the lower ends of the cavities 77 include a shoulder formation 82 where the cavity 77 transitions to the top end of the dispense tip 80. The shoulder formation 82 is configured to receive and support and secure a filter material insert to screen out impurities and any small, non-dissolved excipients or API from the doses that may have been contained in the sample that was taken from the dissolution vessel.

The lower sample well array 78 of the filter plate 75 includes an array of sample wells 81 arranged in a manner that corresponds to the array of dispense tips 80 in the upper filter plate 76. Further, as discussed above a seal member 79 of resilient material is provided on top of the lower sample well array 78. The seal member 79 is preferably an elastomeric material and may be a thermoplastic elastomer or a thermosetting elastomer. In one embodiment of the present invention, the seal member 79 is snapped onto the top of the lower sample well array 78. In an alternative embodiment, the seal member 79 may be molded directly onto the top of the lower sample well array 78 using a method such as a dual shot molding process.

In operation, the samples are each deposited into a dedicated opening in a single cavity 77 at the top of the upper filter plate array 76. After the samples have been deposited, the upper filter plate array 76 as shown in FIG. 17 is lowered onto the lower sample well array 78 as is depicted in FIG. 18. As the upper filter plate array 76 is lowered, the tips of the dispense tips 80 each pierce the seal member 79 over the respective sample wells 81 with which the dispense tips 80 are aligned. Once the upper filter plate 76 is engaged with the lower sample well array 78, compressed air or gas is introduced to the top of each of the cavities 77. The compressed air or gas serves to discharge the sample downwardly through the filter material and through the hollow dispense tip 80 causing each of the samples to be deposited in their respective sample wells 81. After the samples have been deposited, the upper filter plate array 76 is raised to withdraw the dispense tip 80 from the sample well 81 thereby allowing the resilient seal member 79 disposed on the top thereof to return to a closed position effectively sealing the sample well 81 containing the sample.

Turning now to FIG. 19, the MicroSampler 86 is mounted to a mounting assembly such as a plate, wherein positions of the analytical device 83 (shown as an HPLC with a plate transfer apparatus), filter plate and microplate storage means 84, and sample transfer means 85 (depicted as a plate handling robot), are defined and programmed thereto which sampling, transfer, analysis, and resetting are operatively configured. Turning to FIG. 20, the MicroSampler assembly configuration depicted includes a peristaltic pump 91, a compression or vacuum means 93, a plurality of sensors 92, a dispensing assembly 90, a sample flush assembly 89, a filter pre-flush assembly 88, a plurality of mounting brackets 87, a microplate 78 and filter plate 76. The compression or vacuum means 93 is depicted as valves to which compressed air is connected to an indexable assembly wherein after a sample is dispensed in the filter plate assembly, said indexable assembly aligns and compresses said filter plate assembly creating and airtight seal and further delivers pressurized air or gas thereby forcing the dispensed sample into the sample wells of the microplate 78. In the preferred embodiment of the present invention, a plurality of sensors are incorporated to ensure samples are dispensed, pushed through filter plates, and collected in microplates. In addition, a sample flush assembly 89 and filter pre-flush assembly 88 are preferably incorporated. The sample flush assembly 89 is depicted as a trough wherein said trough collects and disposes of fluid that is flushed through sample lines during cleaning cycles or prior to collecting samples in the filter assembly 76. In addition, many APIs and excipients bind filter materials such that it may be required to saturate said filter material with API and excipient prior to collecting a sample for analysis; as such a filter pre-flush assembly 88 is preferably mounted to the Micro-Sampler on a sliding means wherein said pre-flush assembly may be horizontally displaced from said filter. In addition, the pre-flush assembly is preferably configured with a plurality of bores capable of collecting and dispensing to waste samples or portions of sample that are passed through the filters. In addition, the pre-flush assembly may further incorporate a vacuum means for more efficiently collecting samples that are flushed through the filter assembly.

The present invention is believed to represent a significant advancement in the art, which has substantial commercial merit. While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

DRAWINGS

Figure 1:
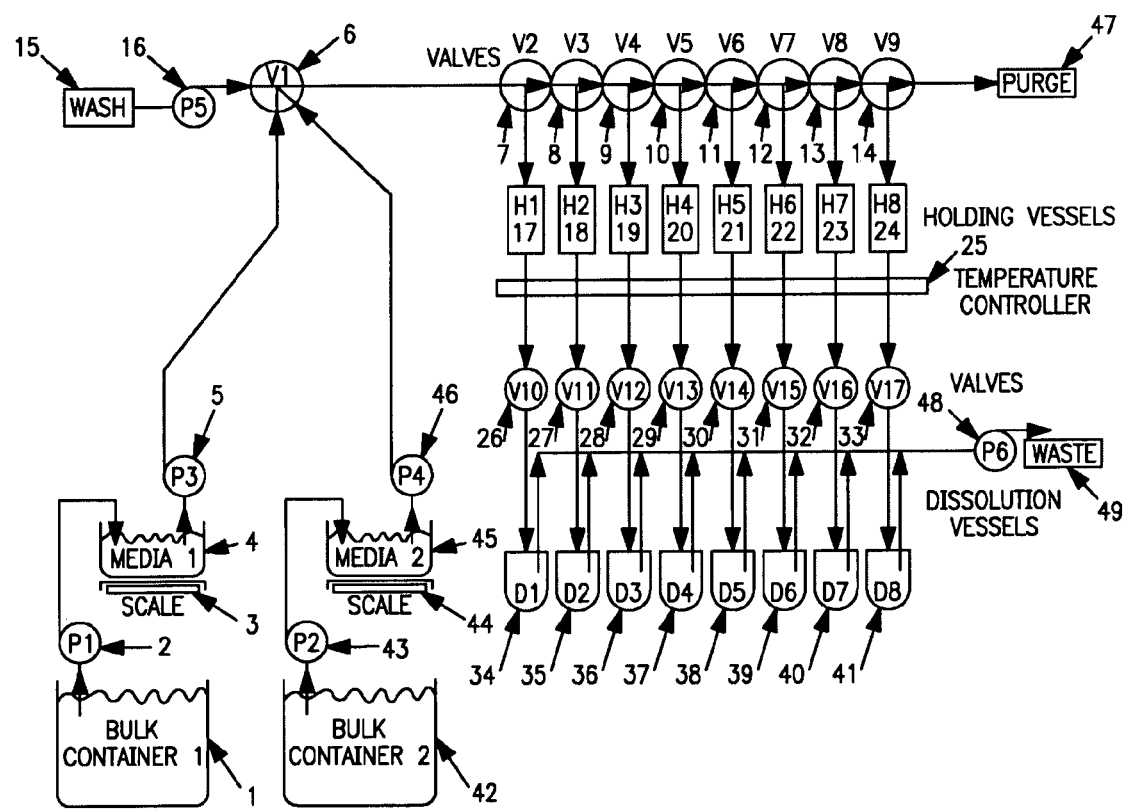
FIG. 1 Depicts a process flow chart detailing the components of the described invention disclosed in the patent.
Figure 2:
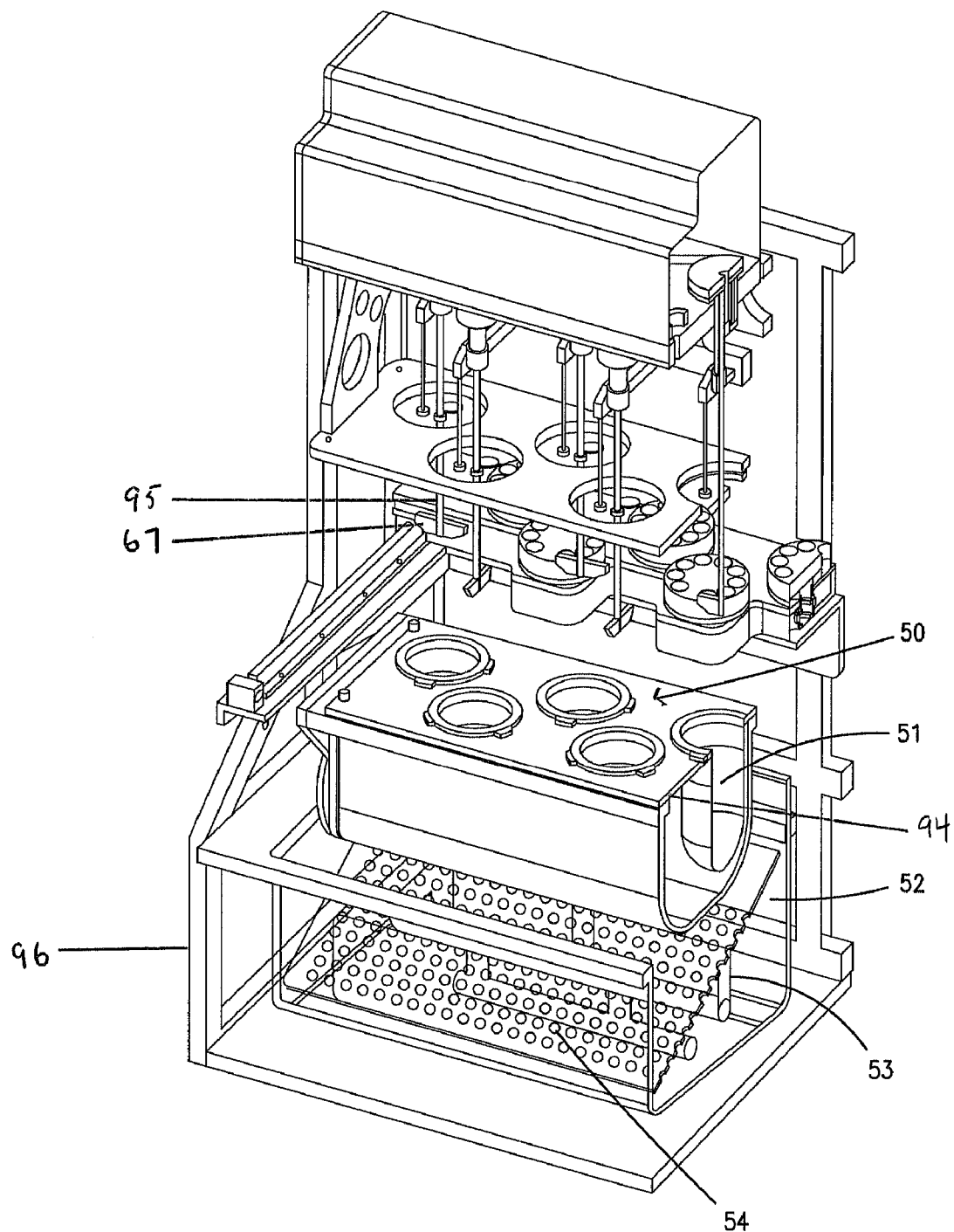
FIG. 2 is a sectional view of the testing assembly of the present invention.
Figure 3:
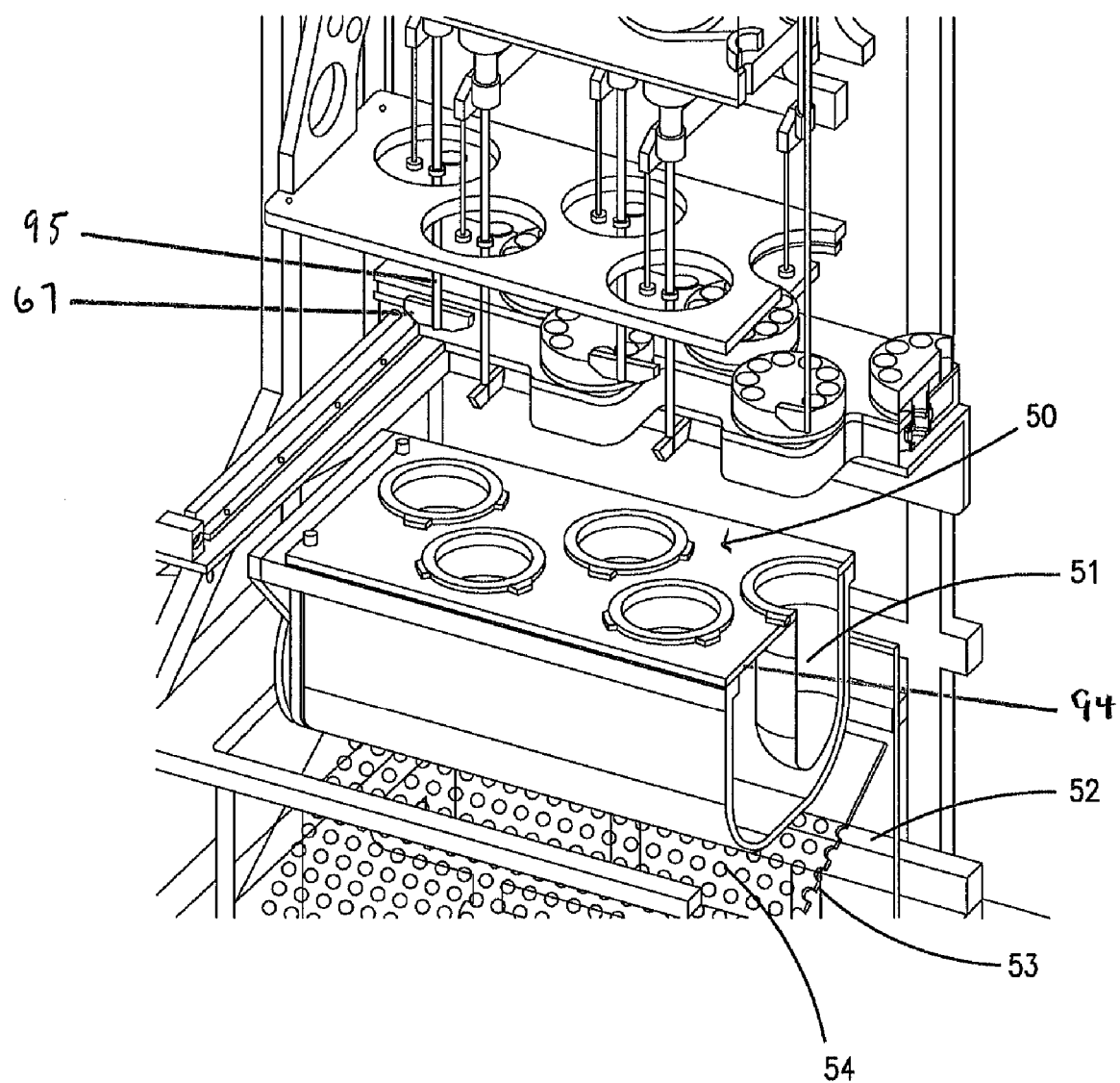
FIG. 3 is an enlarged sectional view of the testing assembly of the present invention.
Figure 4:
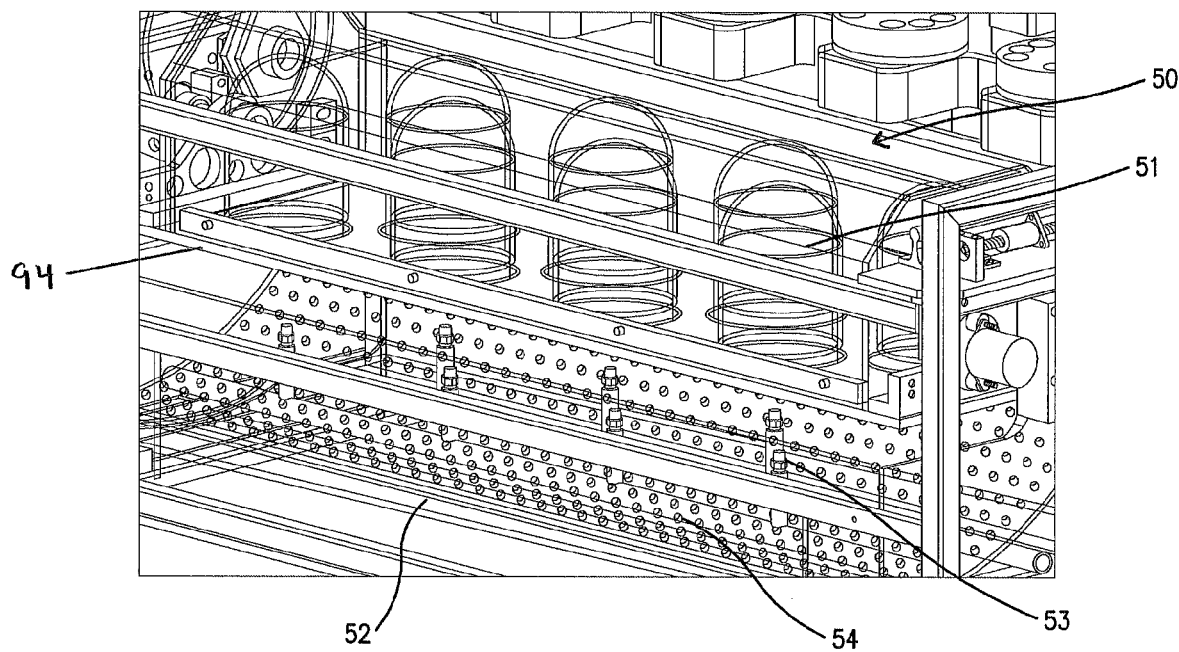
FIG. 4 is an enlarged view of the inverted bath manifold and cleaning manifold mounted on the dissolution system.
Figure 5:
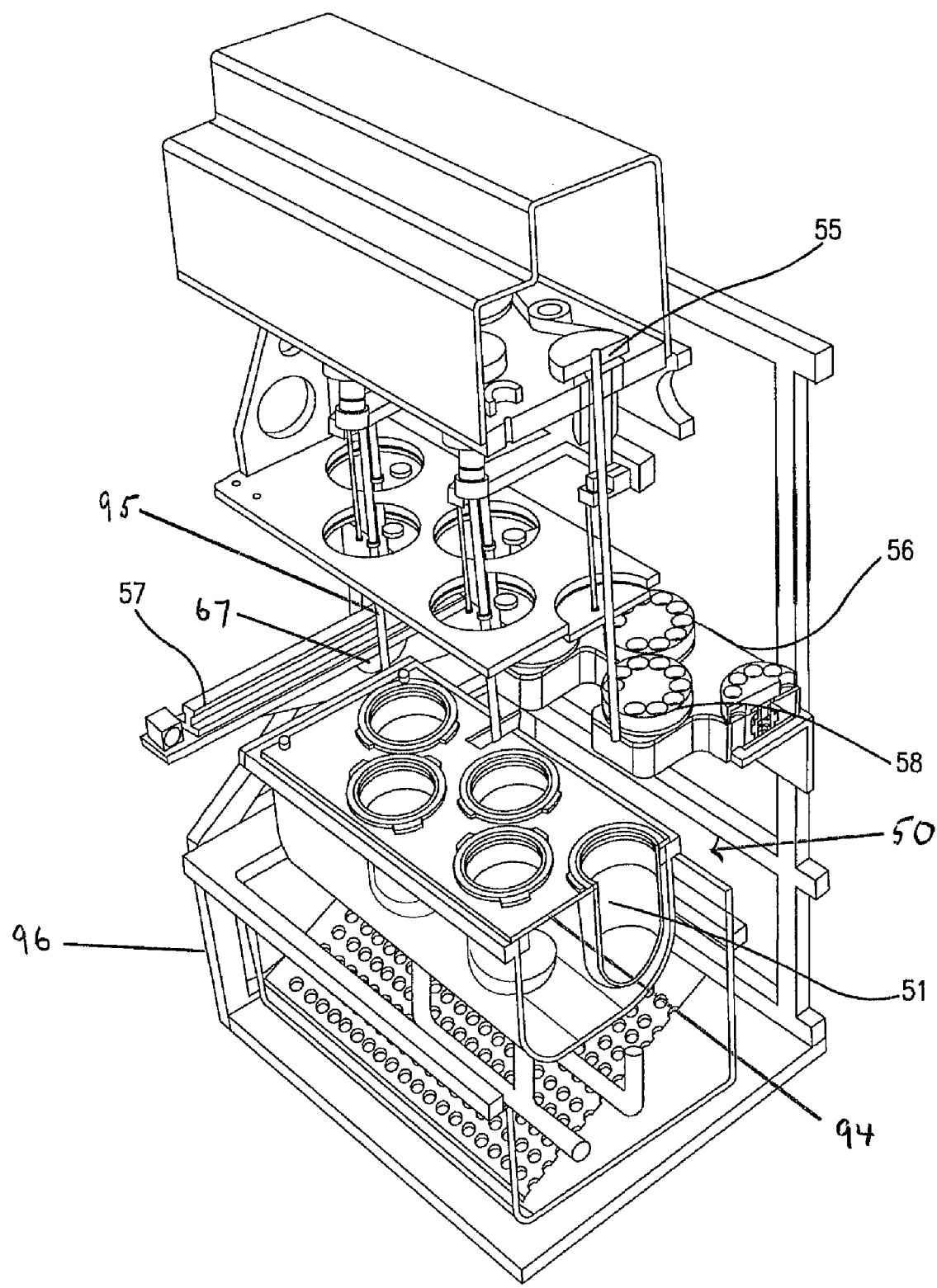
FIG. 5 is a sectional view of the dissolution system detailing components of the dispensing manifold.
Figure 6:
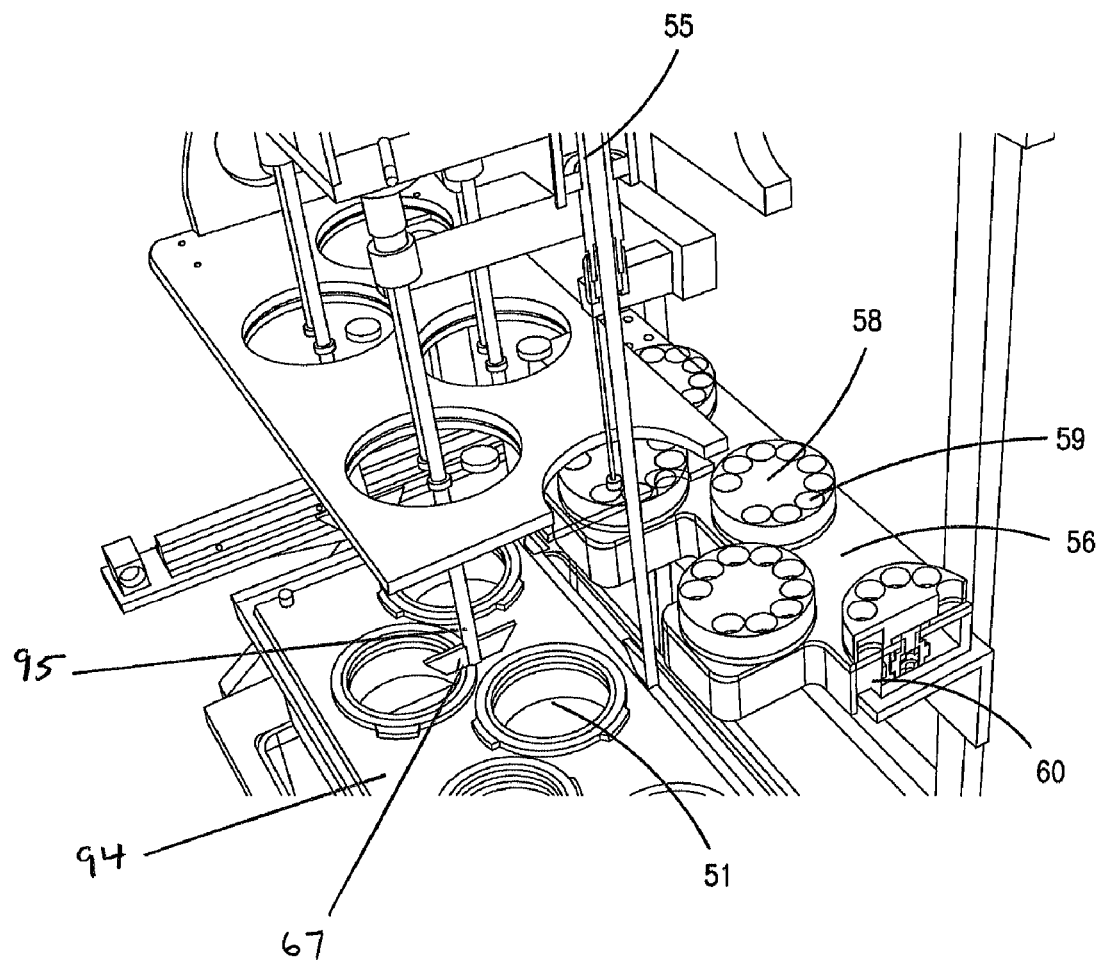
FIG. 6 is an enlarged sectional view of the dissolution system detailing components of the dispensing manifold.
Figure 7:
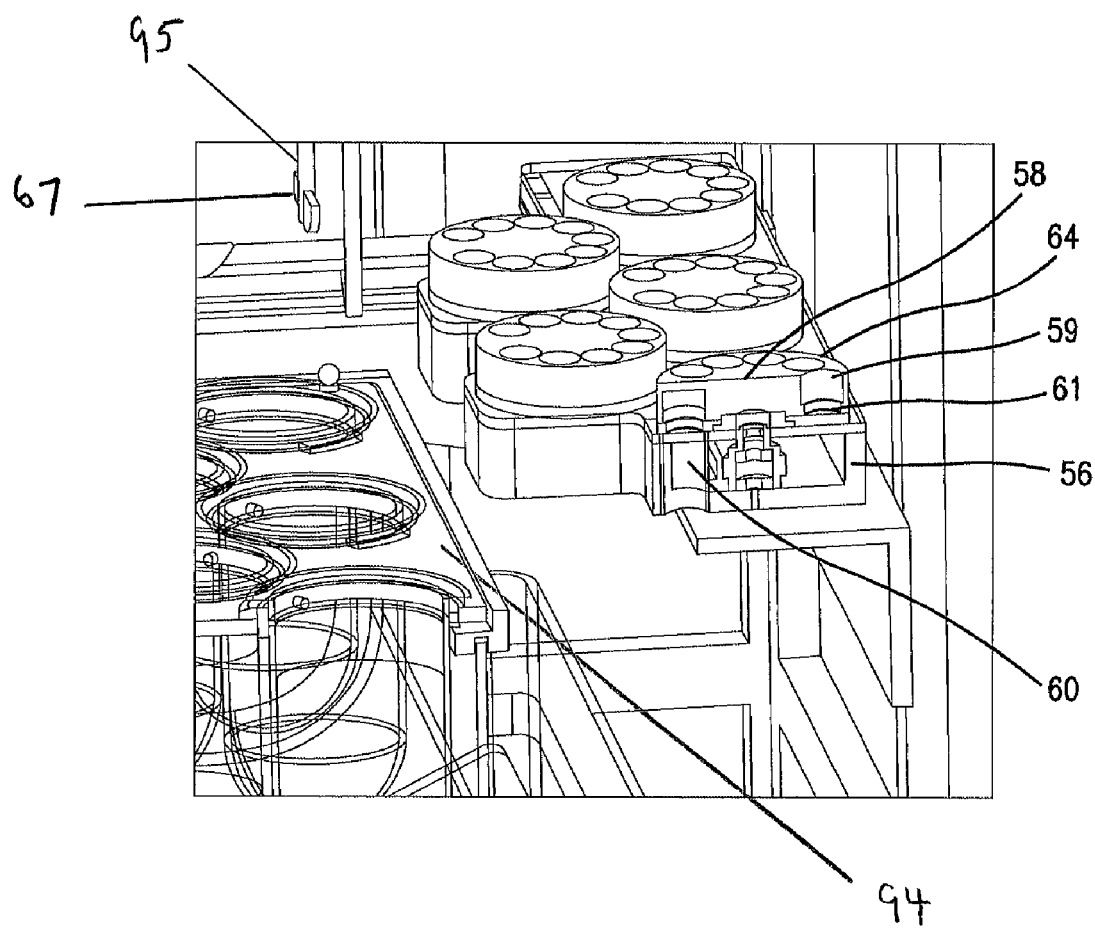
FIG. 7 is an enlarged, lateral sectional view of the dispensing manifold containing a plurality of dosage carousels.
Figure 8:
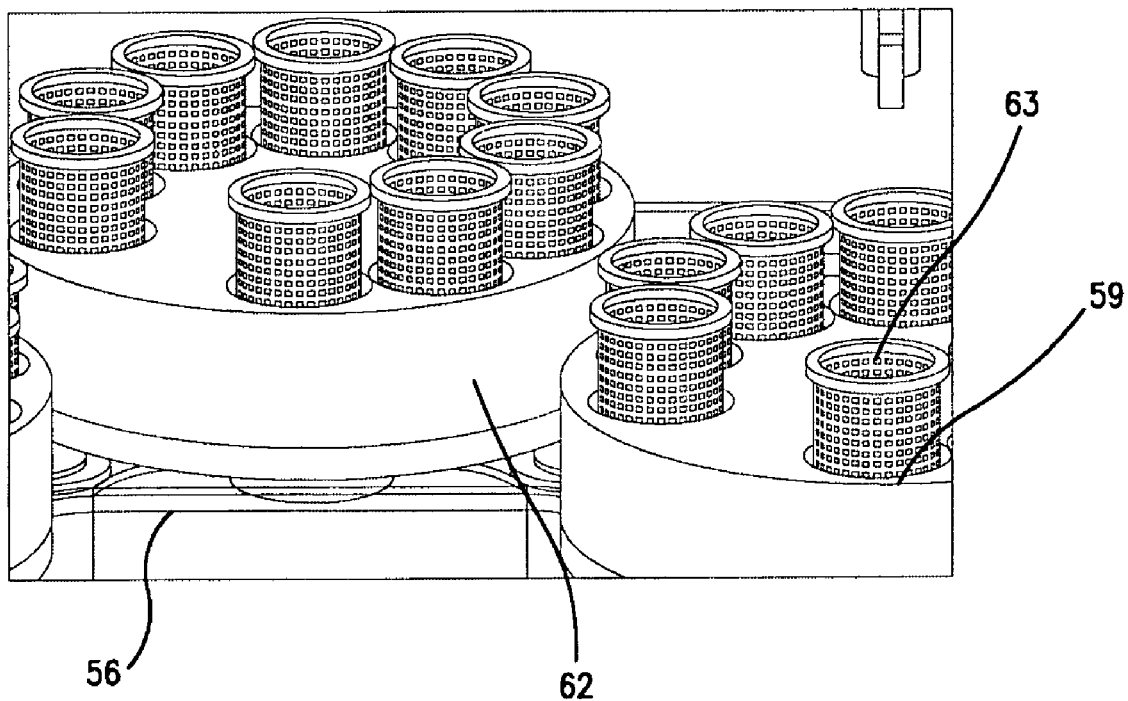
FIG. 8 is an enlarged view of basket carousels that are mounted to the dispensing manifold.
Figure 9:
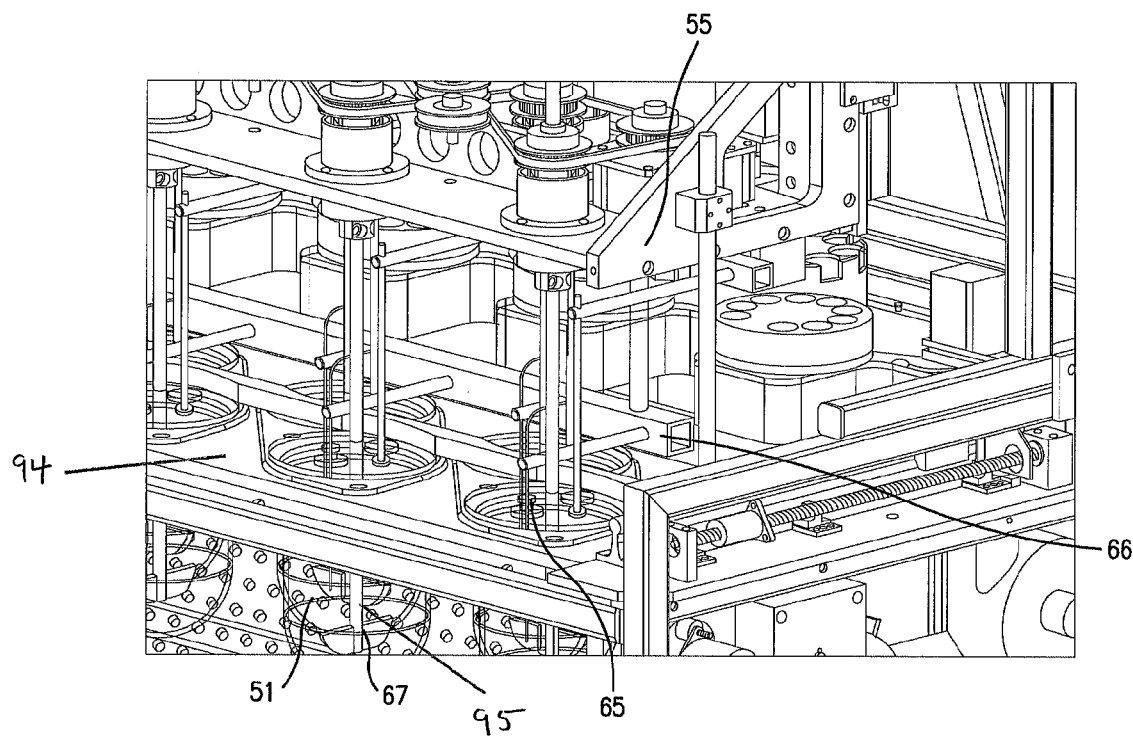
FIG. 9 is a sectional view of a conventional dissolution apparatus.
Figure 10:
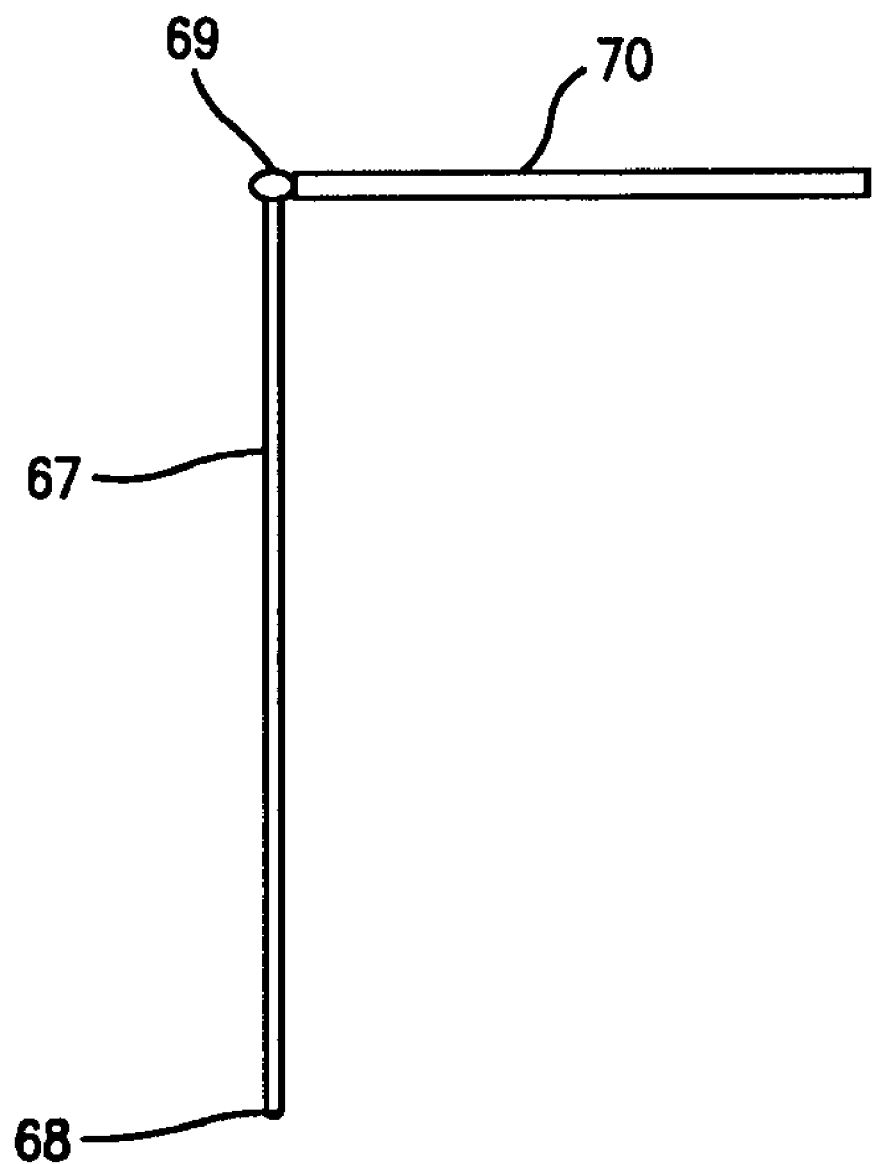
FIG. 10 is a lateral view of the sampling probe.
Figure 11:
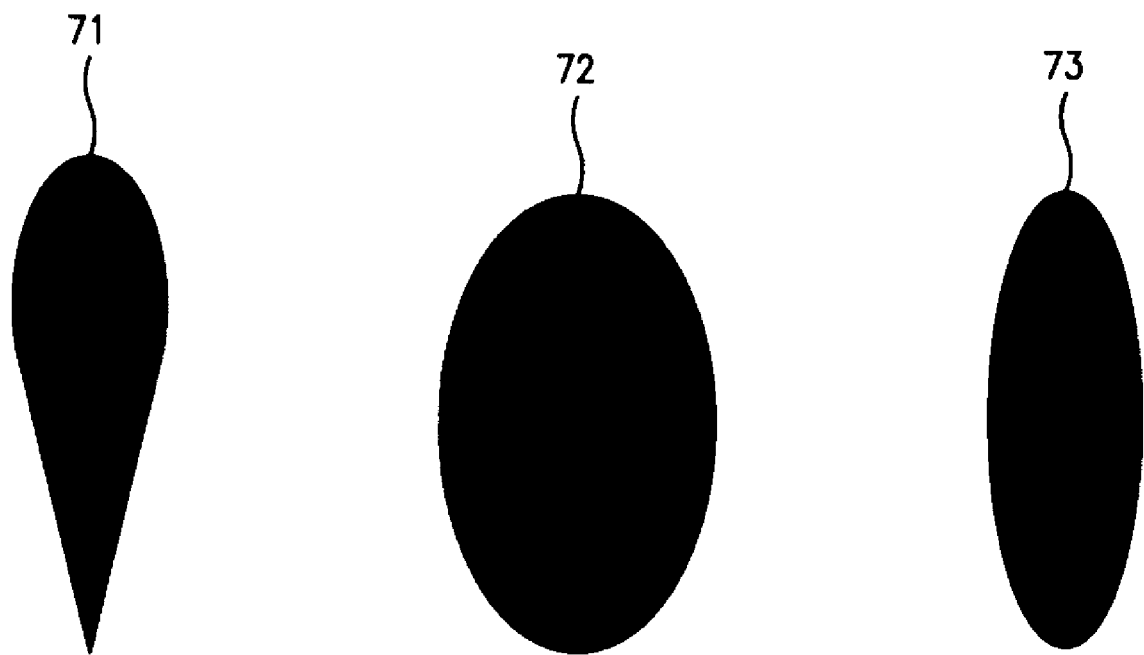
FIG. 11 is a plan view of probe shapes
Figure 12:
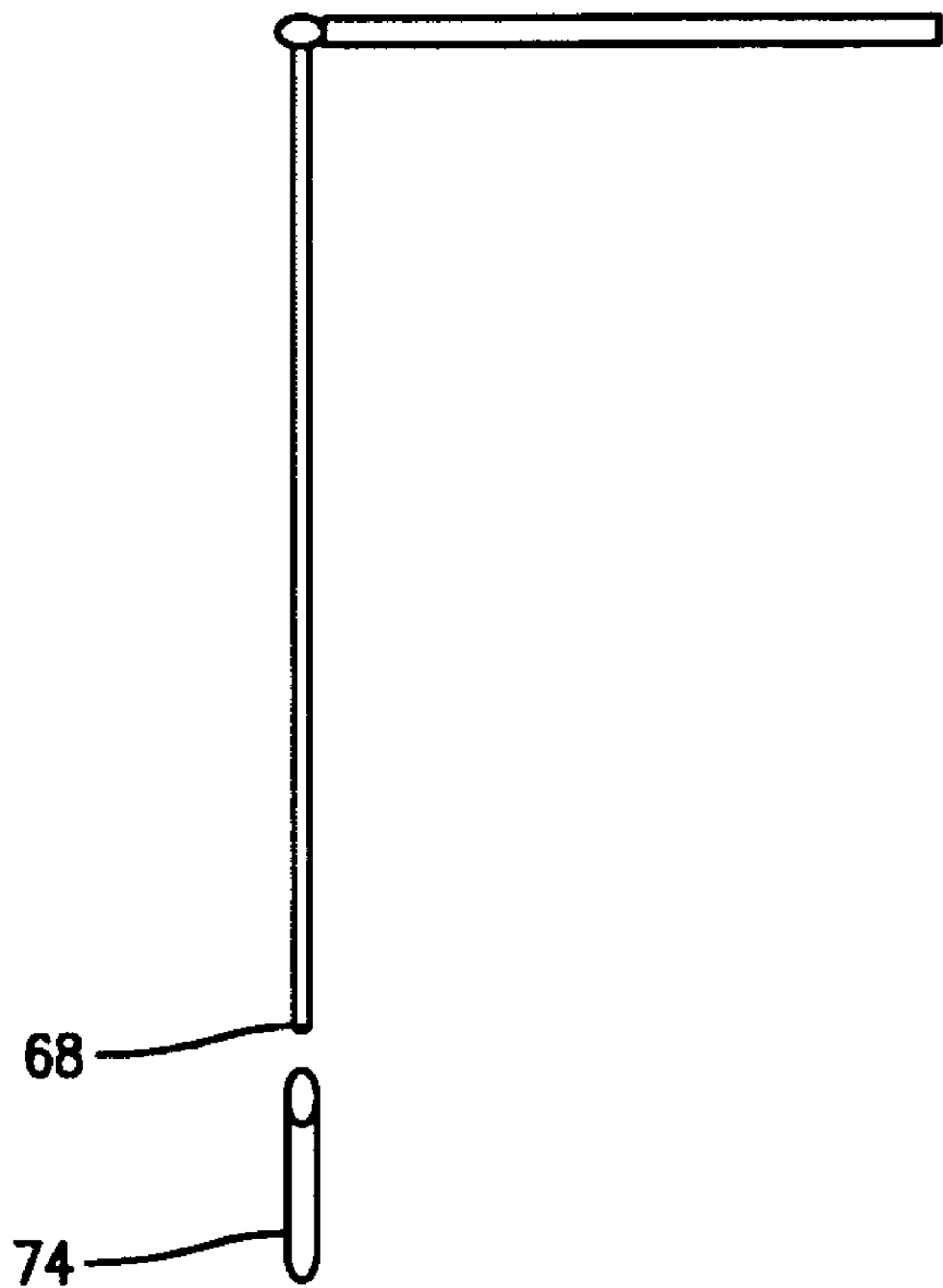
FIG. 12 is a lateral view of the sampling probe and hydrodynamic probe pre-filter.
Figure 13:
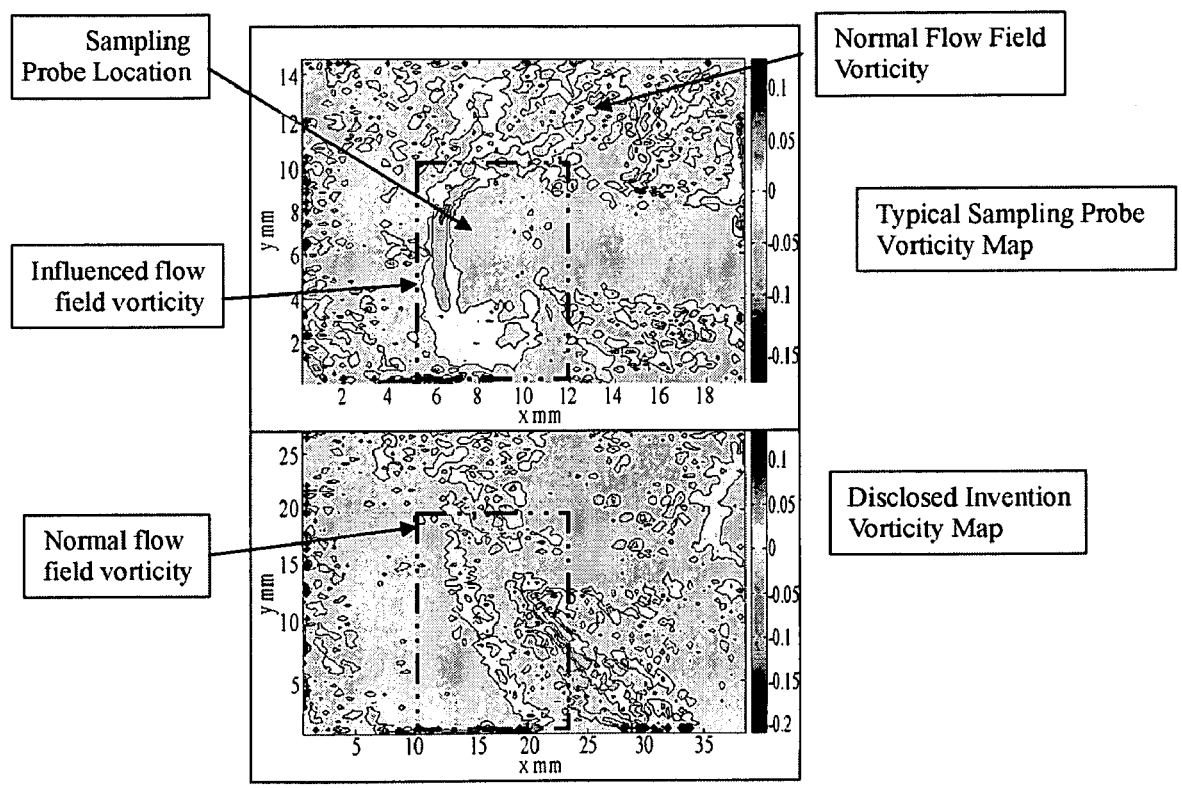
Figure 14:
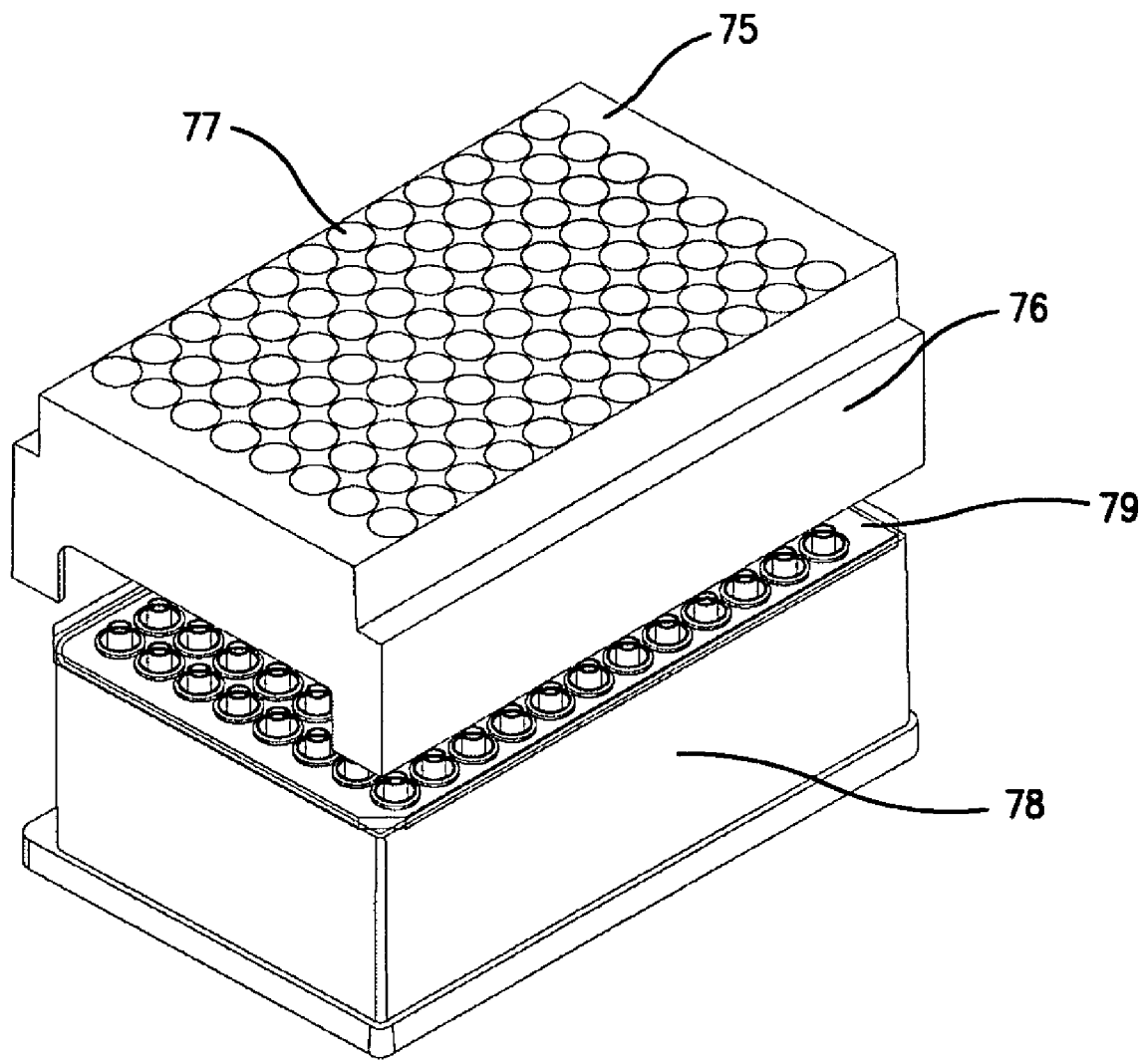
Figure 15:
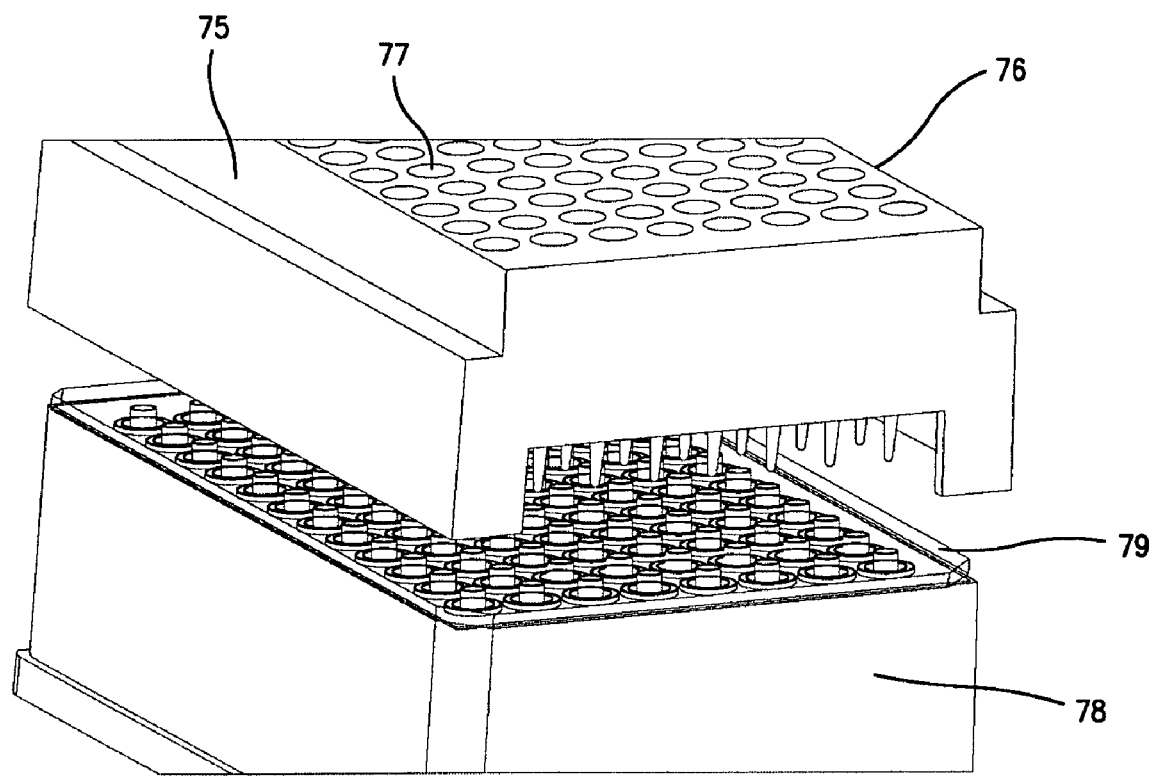
Figure 16:
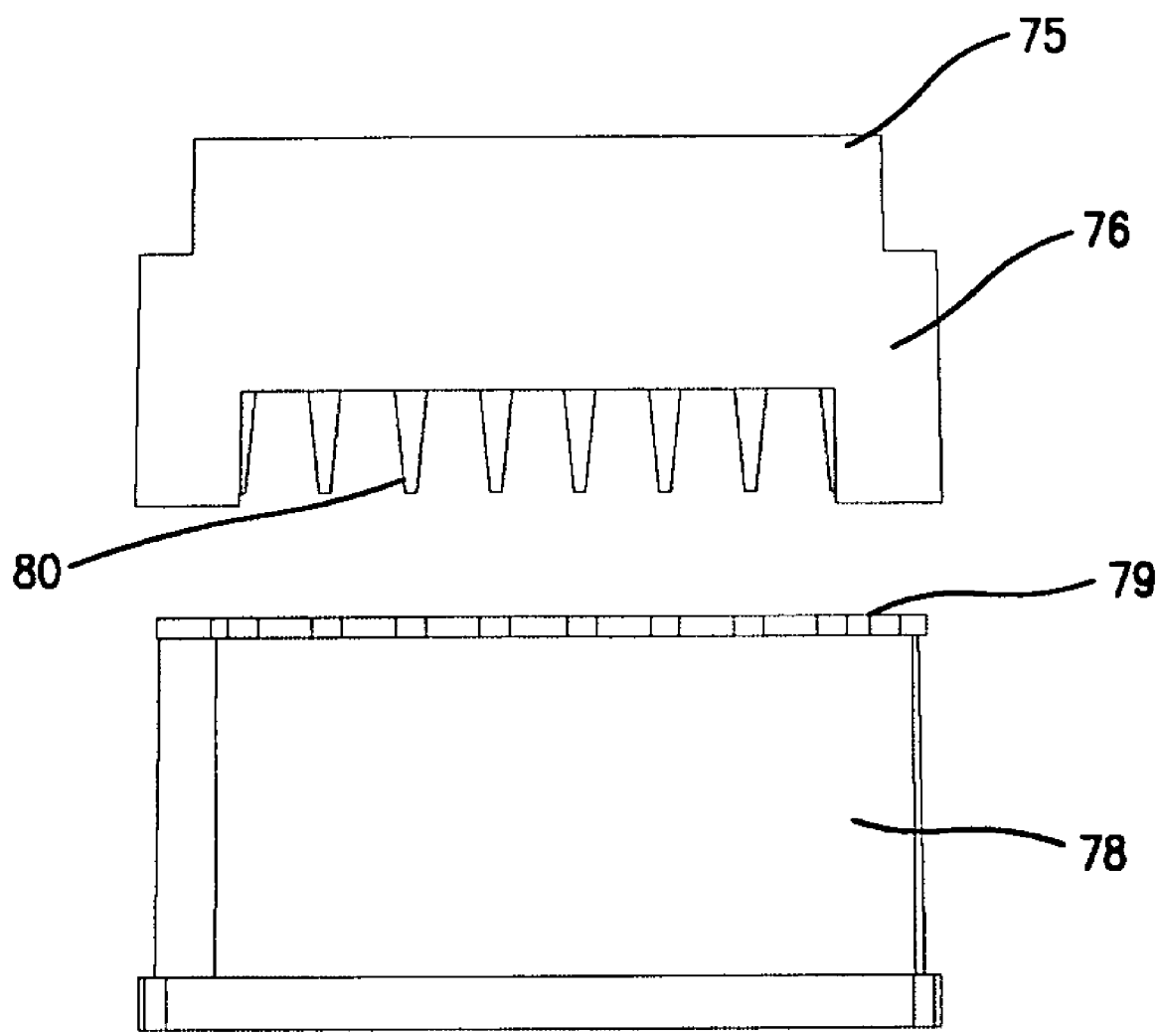
Figure 17:
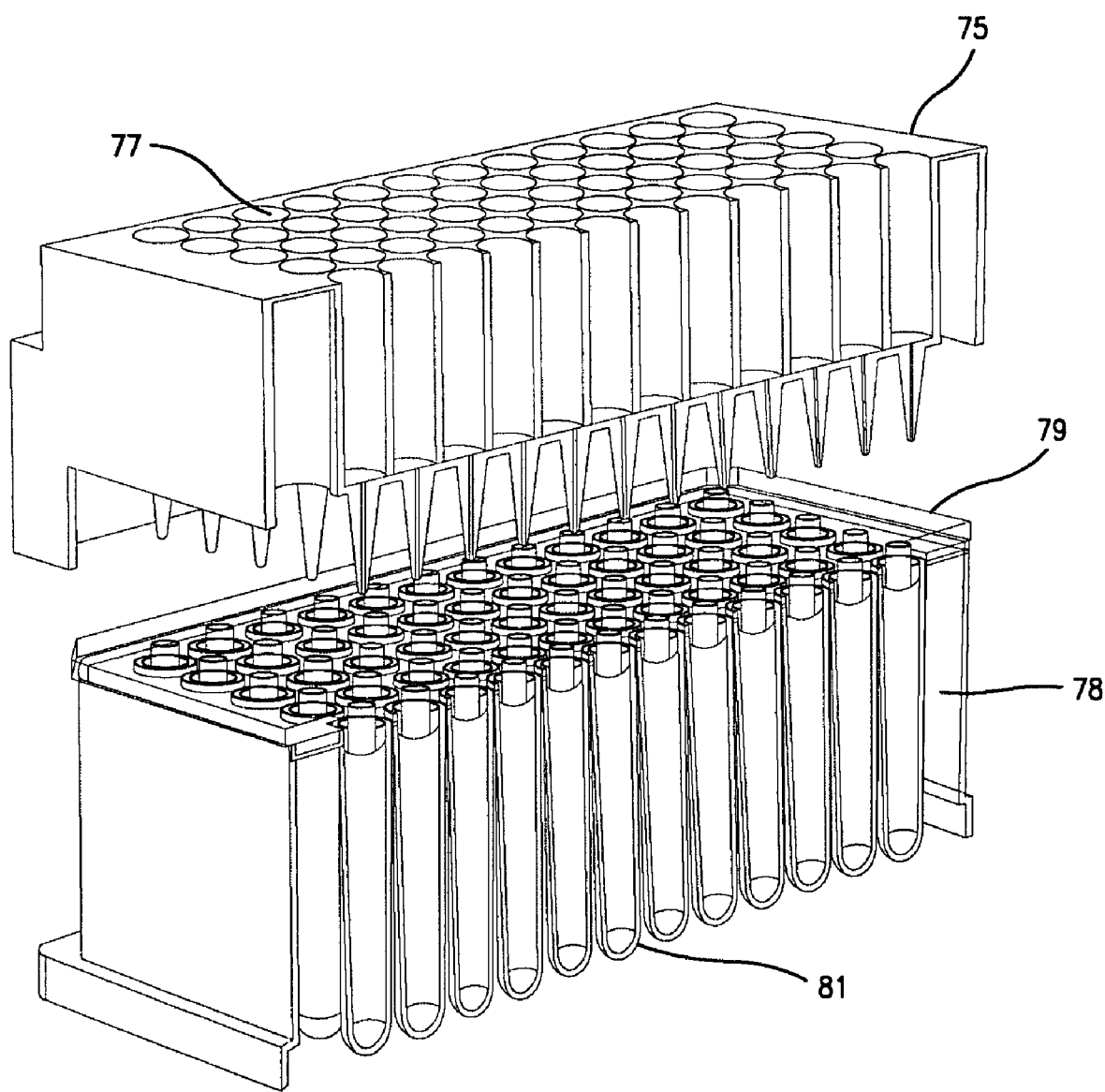
Figure 18:
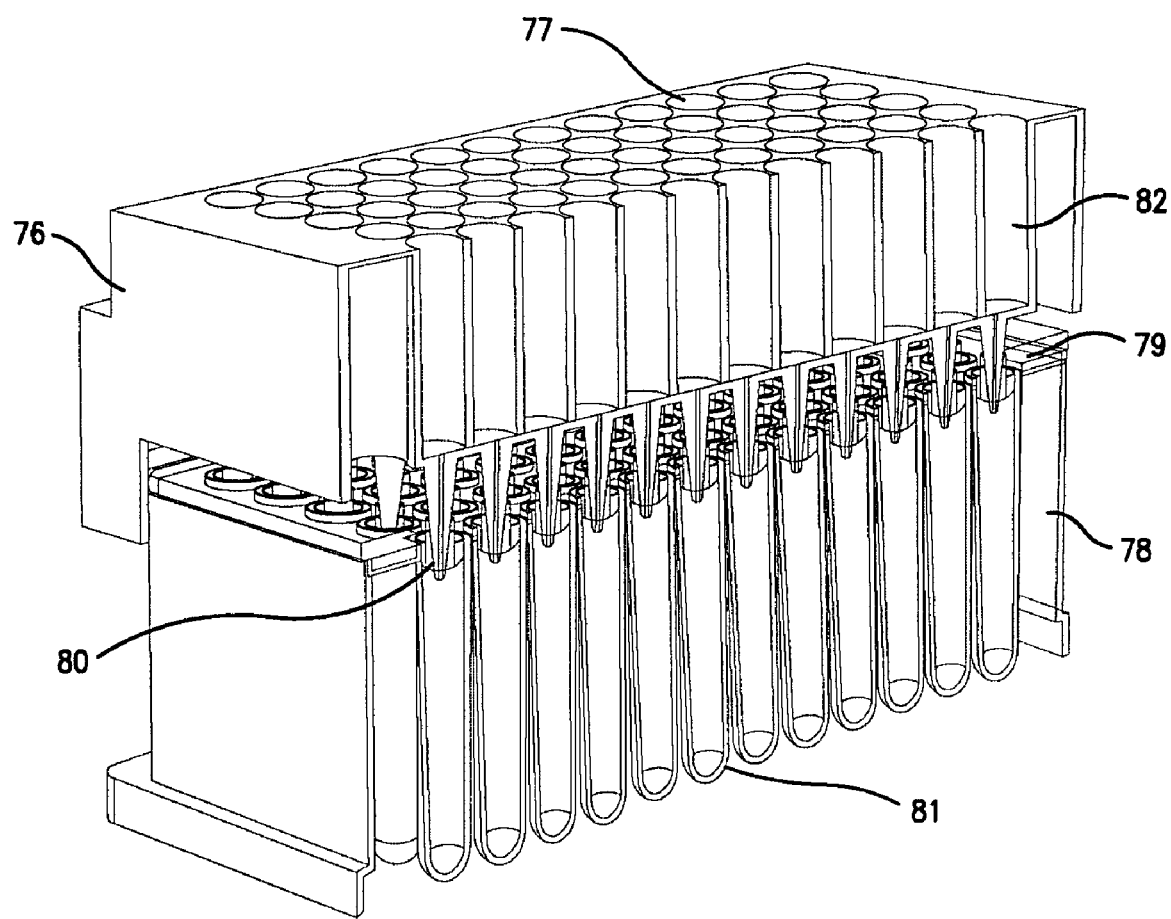

FIG. 13 Data for two dimensional vorticity maps of a conventional sampling probe compared with the disclosed invention FIG. 14 is a perspective view of the filter plate of the present invention;

FIG. 15 is an enlarged perspective view of the filter plate of FIG. 1;

FIG. 16 is an end view of the filter plate of FIG. 1;

FIG. 17 is a cross-sectional view of the filter plate of FIG. 1 with the upper filter plate and the lower collection wells separated; and FIG. 18 is a cross-sectional view of the filter plate of FIG. 1 with the upper filter plate and the lower collection wells engaged.

Figure 19:
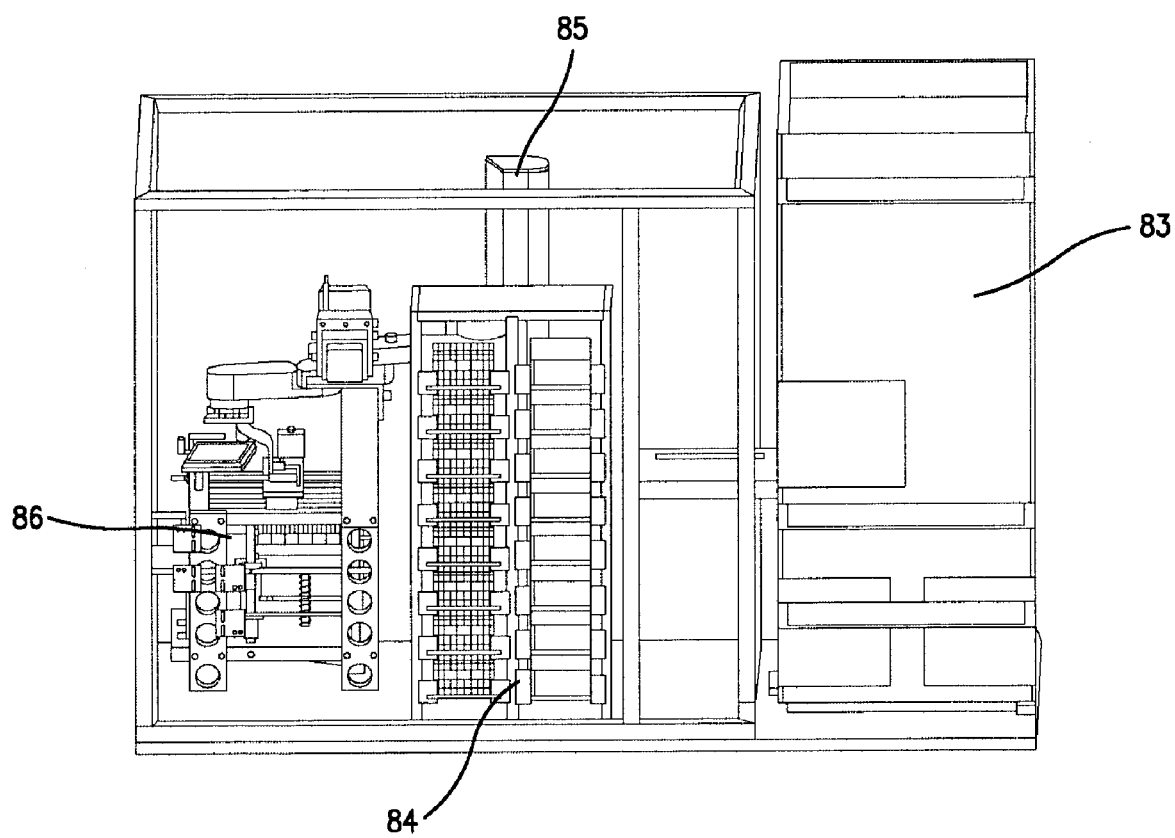

FIG. 19 is an overall view of the main components within the sampling assembly of the disclosed invention.

Figure 20:
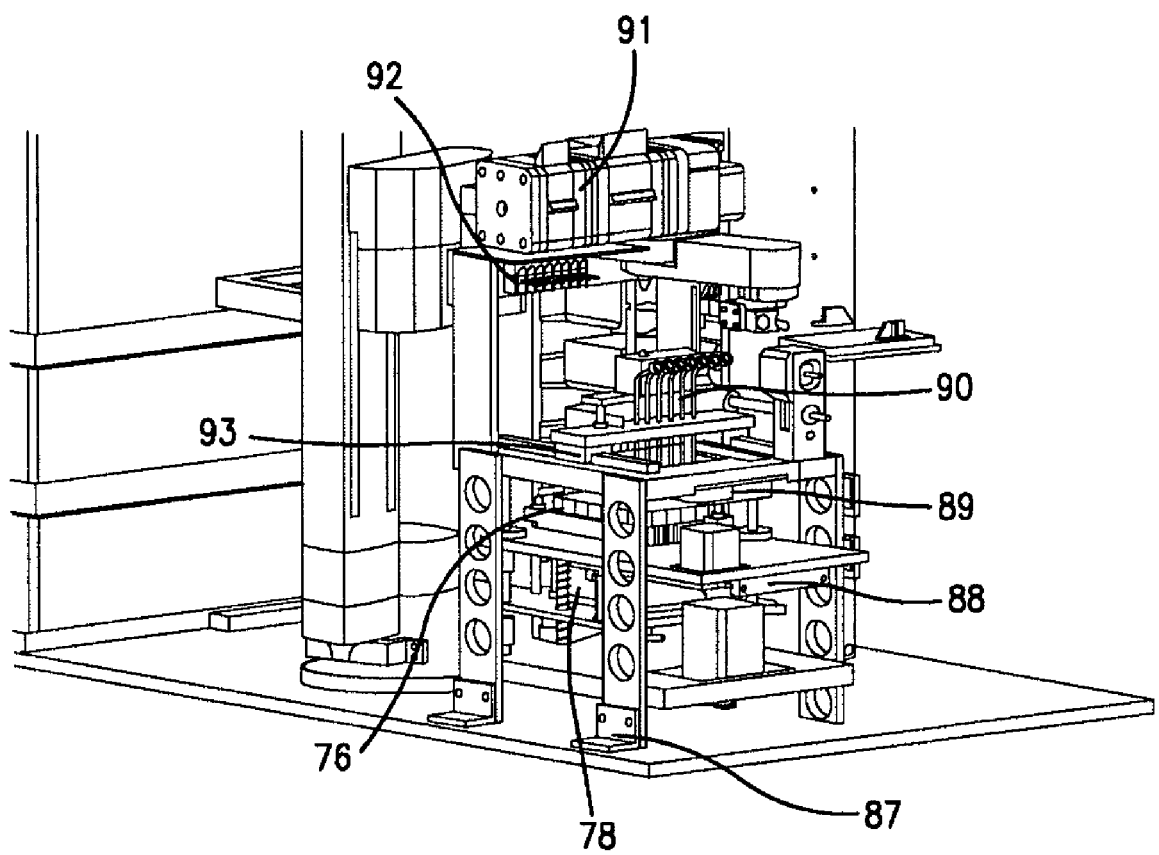

FIG. 20 is an enlarged view of the MicroSampler assembly of the present invention.

What is claimed is:

1. A dissolution testing apparatus, comprising:
   a base structure;
   a vessel support structure configured for mounting a plurality of testing vessels and rotatably mounted to the base structure, wherein the vessel support structure is rotatable from an upright position at which respective open ends of the testing vessels face upwardly to an inverted position at which the open ends face downwardly;
   a cleaning manifold mounted to base structure below the vessel support structure and configured for directing a fluid into the testing vessels while the vessel support structure is at the inverted position; and
   a stirring mechanism comprising a plurality of shafts and movably mounted to the base structure, wherein the stirring mechanism is movable along a vertical direction from a lower position at which the shafts extend into the respective testing vessels to an upper position at which the shafts are outside the testing vessels, and wherein at the upper position the stirring mechanism provides clearance for the vessel support structure to rotate from the upright position to the inverted position.

2. The dissolution testing apparatus of claim 1, comprising a bath manifold, the bath manifold comprising the vessel support structure and a vessel heating device.

3. The dissolution testing apparatus of claim 2, wherein the vessel heating device comprises a heating coil configured to intercalate the testing vessels.

4. The dissolution testing apparatus of claim 2, wherein the vessel heating device comprises a temperature controllable block configured to encase the testing vessels.

5. The dissolution testing apparatus of claim 1, comprising a fluid handling system mounted to the base structure, the fluid handling system comprising a plurality of pumping devices operable to automatically aspirate liquid from a reservoir and dispense the liquid in holding vessels mounted on the base structure, and a plurality of valves configured to control movement of fluid relative to the reservoir, the holding vessels and the testing vessels.

6. The dissolution testing apparatus of claim 1, comprising a non-resident dispensing manifold mounted to the base structure for movement relative to the vessel support structure.

7. The dissolution testing apparatus of claim 6 further comprising a plurality of dispensing nozzles mounted to a ventral side of the dispensing manifold wherein the nozzles operatively dispense fluid within the testing vessels.

8. The dissolution testing apparatus of claim 7 further comprising a plurality of dosage carousels mounted to the dispensing manifold, wherein the dosage carousels comprise a fixed portion comprising a single bore and a rotatable portion comprising a plurality of cavities, the rotatable portion is rotatably mounted to the fixed portion, the carousel is mounted on a dorsal side of the dispensing manifold, and an extended cylinder is inserted into the bore within the carousel operatively such that when the rotatable portion rotates one position a single cavity of the rotatable portion aligns with the bore of the fixed portion.

9. The dissolution testing apparatus of claim 1 further comprising a wash bin disposed below the vessel support structure and a collection grate disposed in the wash bin, the collection grate comprising a plurality of fissures to allow liquid media and dissolved material to flow through the fissures to the wash bin while the vessel support structure is in the inverted position.

10. The dissolution testing apparatus of claim 9 wherein the cleaning manifold comprises a plurality of spraying nozzles extending through the collection grate and positioned to spray fluid into the testing vessels while the vessel support structure is in the inverted position.

11. The dissolution testing apparatus of claim 10 further comprising a plurality of programmable valves configured to enable cleaning of the testing vessels with a variety of fluids and air.

12. The dissolution testing apparatus of claim 8 comprising a plurality of cavities wherein the cavities adopt a cylindrical shape to hold dissolution testing baskets and are rotatably mounted to the dispensing manifold.

13. The dissolution testing apparatus of claim 8 further comprising a basket removal mechanism mounted to the obverse face of the dispensing manifold, wherein the basket removal mechanism operatively forms a clasp around baskets that are attached to basket shafts that are coupled to the stirring assembly and separate the baskets and shafts, and wherein the baskets are gravimetrically displaced into the testing vessels.

* * * * *